(12) United States Patent
Olijve et al.

(10) Patent No.: US 10,155,805 B2
(45) Date of Patent: Dec. 18, 2018

(54) GELATIN PURIFICATION

(71) Applicant: ROUSSELOT B.V., NM Son (NL)

(72) Inventors: Joseph Hubertus Olijve, BR Kaatsheuvel (NL); Bjorn Vergauwen, Lokeren (BE); Paul Stevens, Gent Mendonk (BE)

(73) Assignee: ROUSSELOT B.V., NM Son (NL)

( * ) Notice: Subject to any disclaimer, the term of this patent is extended or adjusted under 35 U.S.C. 154(b) by 0 days.

(21) Appl. No.: 15/531,272

(22) PCT Filed: Nov. 26, 2015

(86) PCT No.: PCT/NL2015/050832
§ 371 (c)(1),
(2) Date: May 26, 2017

(87) PCT Pub. No.: WO2016/085345
PCT Pub. Date: Jun. 2, 2016

(65) Prior Publication Data
US 2017/0342130 A1    Nov. 30, 2017

(30) Foreign Application Priority Data

Nov. 26, 2014   (NL) ..................................... 2013880

(51) Int. Cl.
| | | |
|---|---|---|
| *C07K 14/78* | (2006.01) | |
| *C08B 37/00* | (2006.01) | |
| *C08L 5/00* | (2006.01) | |
| *C08L 89/06* | (2006.01) | |
| *B01J 20/20* | (2006.01) | |
| *C07K 1/34* | (2006.01) | |

(52) U.S. Cl.
CPC ............... *C07K 14/78* (2013.01); *B01J 20/20* (2013.01); *C07K 1/34* (2013.01); *C08B 37/0003* (2013.01); *C08L 5/00* (2013.01); *C08L 89/06* (2013.01)

(58) Field of Classification Search
CPC ............ C07K 1/12; C07K 1/122; C07K 1/34; C07K 2/00; C07K 14/00; C07K 14/47; C07K 14/78
See application file for complete search history.

(56) References Cited

FOREIGN PATENT DOCUMENTS

| | | |
|---|---|---|
| EP | 1829946 | 9/2007 |
| JP | 2004-300077 | 10/2004 |
| JP | 2005-289841 | 10/2005 |
| JP | 2005-289841 A * | 10/2005 |
| WO | 2009/154440 | 12/2009 |
| WO | 2012/031916 | 3/2012 |

OTHER PUBLICATIONS

Sukow et al. Binding of the Triton X Series of Nonionic Surfactants to Bovine Serum Albumin. Biochemistry. 1980, vol. 19, No. 5, pp. 912-917. (Year: 1980).*
International Search Report, International Patent Application No. PCT/NL2015/050832, dated Nov. 26, 2015.

* cited by examiner

*Primary Examiner* — Jeffrey E. Russel
(74) *Attorney, Agent, or Firm* — Casimir Jones, S.C.; Tanya A. Arenson

(57) ABSTRACT

Described is an improved method of removing lipopolysaccharide from an aqueous medium comprising gelatin and lipopolysaccharides, the method comprising the steps of providing an aqueous medium comprising gelatin and lipopolysaccharides, adding to the aqueous medium a micelle-forming surfactant, contacting the medium with a solid adsorbent, separating the solid adsorbent of from the medium and recovering the aqueous medium comprising the gelatin, wherein the method is performed at conditions below the cloud point of the surfactant.

15 Claims, 2 Drawing Sheets

GELATIN PURIFICATION

The invention relates to a method of removing lipopolysaccharide from an aqueous medium comprising gelatin and lipopolysaccharides and to gelatin having a low lipopolysaccharide content.

Gelatin is a mixture of water-soluble proteins derived from collagen. Gelatin is obtained e.g. by partial hydrolysis of collagen, obtained by aqueous extraction of skin, tendons, ligaments, bones etc. in acid or alkali conditions, or by enzymatic hydrolysis. Gelatin obtained by acid treatment is called Type A gelatin, whereas Type B gelatin is derived from alkali based process.

Gelatin does not constitute a uniform protein molecule, but comprises a variable amount of protein molecules of variable length, having an average molecular weight of up to 200-250 kDa. Therefore, the molecular weight distribution of gelatin is an important parameter responsible for or determining often critical and important gelatin properties such as viscosity and bloom value, or gel strength.

Gelatin forms a thermoreversible gel at room temperature, and dissolves in hot water. Gelatin is commonly used in diverse industries, for example in food, pharmaceuticals and cosmetics applications, among others as gelling agent and texturizer in e.g. fruit gums and gelatin desserts, but also finds application in the medical field, e.g. for plasma substitution and gelatin based implants.

The molecular weight varies among others due to different extraction temperatures and conditions. As a result also bloom and viscosity will also vary. Temperature is an important parameter in gelatin preparation, e.g. purification conditions before the gelatin can be applied in food, pharmaceutical, technical and medical applications and often needs careful control. When it comes to use of gelatin, in applications where gelling characteristics and viscosity are important, a temperature of 60° C. is considered as maximum handling temperature, although temperatures of up to e.g. 62° C. or 65° C. for a limited time period of e.g. 5 or 10 to 30 or 45 min. may be acceptable under circumstances when some loss of gelling capacity and/or viscosity is tolerated. At temperatures above 65° C., in particular above 70° C., undesired hydrolysis of gelatin occurs, i.e. breakdown of protein molecules to smaller peptides, resulting in a lower gel strength or even loss of gelling capacity. Accordingly, so-called 'hydrolysed gelatin' is a peptide preparation originating from hydrolysis of gelatin to peptide molecules having an average molecular weight of 70 kDa or less, usually 20 kDa or less, usually between 100 and 15000 Da. Because of the relatively small molecules, hydrolysed gelatin has no jellifying properties. Hydrolysed gelatin is e.g. used as texture conditioner and moisturizer in topical crèmes, and is also used in nutritional products because of the high glycine, proline and hydroxyproline content and is associated with health effect but can also be used for biomedical applications. It is also named 'hydrolysed collagen', as collagen is first hydrolysed to gelatin and then further to the non-gelling hydrolysate.

The molecular weight distribution of gelatin is usually measured by size exclusion HPLC (high performance liquid chromatography) techniques, and eluted fractions are detected by UV adsorption and the measured data are evaluated by suitable software, all techniques, known in the art, see e.g. Olijve et. al., Journal of Colloid and Interface Science (2001) 243, 476-482. For hydrolysed gelatins with an average molecular weight smaller than 70 kDa, such as smaller than 20 kDa, the same method can be used, but it preferred to use a separation column, such as TSKgel2000SWXL (Tosoh BioScience, Japan), to obtain high resolution (Zhang et. al., Food Hydrocolloids 23 (2009) 2001-2007).

Viscosity of gelatin (the dynamic viscosity) is usually measured by measuring the flow time of a 6.67 w/w % solution of gelatin through a standard flow pipet at 60° C., see GME Monograph Standardized Methods for the testing of Edible Gelatin, version 10, 2014 (GME, Brussels, Belgium), herein also referred to as 'GME10', chapter 2.4.2, p. 81-86.

The gel strength of a 6.67 w/w % gelatin gel can be determined by standardized apparatuses (see GME10), such as a QTS 25 Texture Analyzer (Brookfield Viscometers) or a Texture Analyzer TA-XT2 (Stable Micro Systems Ltd., London, United Kingdom), and is indicated by a bloom number (also referred herein as 'bloom value', see GME10).

In gelatin preparation processes, raw materials are often contaminated by bacteria and as a result, common gelatin preparations can comprise lipopolysaccharides (LPS).

Lipopolysaccharides are found in the outer membrane of Gram-negative bacteria and are potential toxins. LPS are also known as "endotoxins" as lipopolysaccharides are not secreted by bacteria but are part of the membrane structure. Lipopolysaccharides are therefore mainly released after death and lysis of the bacterial cell.

LPS consist of a variable polysaccharide chain and a lipid moiety, lipid A. LPS molecules are about 10 kDa in size, but can form large aggregates in aqueous media, also named "micelles" having a molecular weight of up to 1000 kDa.

LPS are toxic to most mammals and the animal host will often suffer from a wide spectrum of non-specific pathophysiological reactions, such as fever, tachycardia, organ dysfunction and even death.

Although a certain LPS content can be tolerated in many gelatin applications, specific applications, such as for medical purposes (e.g. like gelatin based plasma substitution, devices and implants) the endotoxin level should preferably be lower than 20, preferably 10 EU/g or even less. For example USA governmental regulations of the Food and Drug Administration (FDA) allow a maximum of 0.5 EU/ml or 20 EU/device for products that are in contact with the cardiovascular and/or lymphatic system. For devices in contact with cerebrospinal fluid the limit is even 0.06 EU/ml or 2.15 EU/device (~2 EU/g gelatin). For devices that are in direct or indirect contact with the intraocular environment an even lower endotoxin limit may apply.

The *Limulus* assay (LAL) is a well-known bioassay in the art to measure up to sub-picogram quantities of LPS. *Limulus* amebocyte lysate (LAL) is an aqueous extract of blood cells (amoebocytes) from the horseshoe crab, *Limulus polyphemus*. LAL reacts with bacterial endotoxin or lipopolysaccharide (LPS), which is a membrane component of Gram negative bacteria. This reaction is the basis of the LAL test, which is then used for the detection and quantification of bacterial endotoxins. A US-FDA, USP 2011, chapter <85> accepted recommended LAL method to quantify the LPS levels is the chromogenic Endosafe method, e.g. from Charles River USA. Other accepted and recommended methods are the EndoZyme recombinant factor C method from Hyglos GmbH (Germany). Both said methods result in similar or identical measurement values and can therefore be used interchangeably.

In the art, methods for reducing the LPS content from protein solutions using detergents such as TRITON are e.g. described by Hirayama and Sakata, Journal of Chromatography B, 781 (2002) pp. 419-432. The detergents are described to release endotoxin monomers from the micelles which monomers will be adsorbed by the adsorbents. However, Hirayama and Sakata warn for the use of non-selective adsorbents such as activated carbon and anion-exchangers when removing endotoxin from a protein-containing solution since not only the endotoxin but also the proteins tend to bind to said non-selective adsorbents.

WO 2009/154440 describes a method for the reduction of LPS content in a LPS containing biopolymer material such as an aqueous alginate or gelatin solution. The method in WO 2009/154440 relies on the use, in the said solution, of a surfactant, a solid adsorbent, and on an increase in the temperature of the said solution to above the cloud-point of the surfactant used, resulting in the loss of solubility and aggregation of the surfactant and thereby into a 3 phase extraction process wherein both aggregated surfactant as well as the LPS, bound to the adsorbent are removed from the aqueous phase comprising the purified biopolymer by centrifugation. For this purpose, it is critical that the solution is brought to conditions such, that the temperature of the solution comprising the biopolymer, surfactant, adsorbent and the LPS is above the cloud point temperature of the surfactant at that conditions, in order to allow the surfactant to aggregate so that the aggregates can be removed, together with the LPS adsorbed to the adsorbent, by centrifugation.

Accordingly, WO 2009/154440 describes the preparation of an aqueous alginate solution comprising TRITON X-114 (

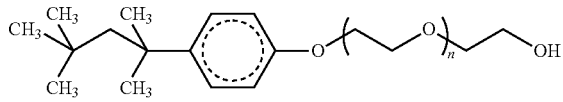

whereby n=on average 7.5; having a cloud point of 23° C.) and a solid adsorbent at a temperature just below the cloud point, followed by heating to 70° C., i.e. well above said cloud point, to form aggregates of the surfactant. Both aggregates and adsorbent were precipitated by centrifugation, resulting in an aqueous alginate phase with decrease LPS content. Also, the preparation of a gelatin solution is described comprising TRITON X-100 (

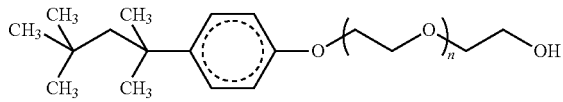

whereby n=on average 9.5; having a cloud point of 68-69° C.) and activated carbon as adsorbent, again just below the cloud point temperature, followed by heating to 90° C. to induce phase separation, i.e. formation of aggregates of the surfactant. By centrifugation, the aggregated surfactant and the activated carbon, whereto LPS was bound, were precipitated. However, heating at above the cloud point of TRITON X-100, i.e. at 70° C. or higher, in casu 90° C., results in significant hydrolysis of the gelatin, and an intrinsic loss of functionality such as viscosity and gel strength. At such high temperatures, also undesired discoloration of the gelatin can occur due to Maillard reactions in the gelatin. In the teaching of WO2009/154440, the gelatin is destroyed by the heating step and a gelatin hydrolysate is produced, i.e. not capable to gel. Further, the centrifugation step makes industrial application of said method difficult.

JP 2005/289841 describes a method for producing gelatin type B with reduced endotoxin content. The method comprises treating an animal tissue with a solution of calcium hydroxide and a quaternary ammonium salt at a pH of 12 for at least 5 days. At such basic conditions, deamination of the gelatin takes place, resulting in a decrease in isoelectric point to 5-6, i.e. only gelatin of type B can be obtained. Subsequently, the gelatin solution is neutralized to a pH of about 4.5-5 with acid, and gelatin is obtained by extraction at a temperature of at least 65° C. The gelatin thus obtained can further be sterilized by filtration through a 0.2 micrometer membrane containing less than 5 EU/g of endotoxins. However, this method is not suitable for large gelatin molecules having a molecular weight above 200 KDa because of the pore size of the membrane used in the filtration step.

JP 2004/300077 describes a method for removing endotoxin from collagen protein comprising subjecting said protein to a basic alcohol and/or acetone treatment at a pH of 10-12, therewith decomposing the endotoxin contained in the collagen protein. The resultant protein having less than 1000 EU/g LPS are recovered by precipitation. At such high pH values, the isoelectric point of the protein will drop to about 5-6 as a result of deamination.

EP 1829946 describes a method for reducing the endotoxin content of gelatin by subjecting gelatin solutions having an average molecular weight of up to 100,000 Da to ultrafiltration. Although this document describes the possible use of membranes having a cut off of 300,000, gelatins of such size cannot efficiently be processed this way because of the viscosity of the solution. Only very diluted solutions of such gelatins may be subjected to ultrafiltration, rendering the method very inefficient and expensive. By ultrafiltration, only gelatins having an average molecular weight of 100,000 Da or less have been shown to be suitable and described for ultrafiltration.

WO 2012/031916 describes a method for reducing the endotoxin content of insoluble collagen to less than 10 EU/g, comprising treating the collagen with aqueous alkali, acid and an oxidizing agent without dissolving the collagen.

The present inventors have now surprisingly found that LPS can very effectively be removed from aqueous gelatin preparations, without the need of an ultrafiltration or centrifugation step, using a micelle forming surfactant such as TRITON X-100, under non hydrolyzing conditions for the gelatin, without the need to form insoluble aggregates of the surfactant to enable efficient removal thereof. It has now been found that removal LPS from gelatin solutions can be effected using a micelle forming surfactant under conditions that are below the cloud point of the said surfactant, resulting in even improved reduction of LPS as compared with the above cloud point extraction technique. Without the wish to be bound to any explanation, it is believed that effective adsorption of the surfactant and LPS by a solid adsorbent, such as active coal, is surprisingly not dependent on insoluble aggregate formation of the surfactant, therewith rendering temperature elevation after the step of allowing the surfactant to interact with the LPS in the medium to above the cloud point of the surfactant superfluous, therewith enabling removal of LPS under more gentle conditions. Accordingly, a method is provided that is suitable for removal of LPS from gelatin under non-hydrolyzing conditions, keeping the properties of the gelatin such as viscosity substantially intact as compared to the gelatin before the LPS removal.

To this end, the invention provides a method of removing lipopolysaccharide from an aqueous medium comprising gelatin and lipopolysaccharides, said method comprising the steps of:

1) providing an aqueous medium comprising at least 2 w/w % gelatin and lipopolysaccharides,
2) adding to the aqueous medium 0.01-1.5 w/w % of a micelle-forming surfactant,
3) contacting the medium of step 2) with a solid adsorbent,
4) separating the solid adsorbent of step 3) from the medium,
5) recovering the aqueous medium comprising the gelatin, wherein each of the steps 1)-5) are performed at a temperature of 68° C. or less, said temperature being below the cloud point of the micelle-forming surfactant, at least steps 2) and 3) being performed at a temperature of at least 30° C.

The term "aqueous medium" is intended to encompass water, mixtures of water miscible solvents and water, wherein water is predominantly present, and any solution wherein water or such mixture is the solvent. The medium is however preferably void of water miscible solvents. The aqueous medium can comprise any type of gelatin, e.g. type A of type B gelatin, of e.g. bovine, porcine, poultry or fish origin. There are no restrictions to the bloom, molecular weight and viscosity values of the gelatin wherefrom LPS is to be removed. In particular, the gelatin is dissolved in the aqueous medium, e.g. by mixing the gelation with the solvent, e.g. water, at room temperature or elevated temperature, but preferably not above 68° C., preferably not above 65° C., more preferably not above 60° C. in order to avoid hydrolysis of the gelatin, for about 30 to 60 minutes to allow the gelatin to swell, resulting in the medium being a gelatin solution. At or below 60-68° C. thermal hydrolysis of gelatin and possible undesired chemical reactions are avoided, so that the properties and functionality of the gelatin, such as bloom value, average molecular mass and viscosity, remain intact as compared with the gelatin as provided in step 1). Herein, the functionality is defined to remain intact when the molecular weight of the gelatin does not decrease, as a result of the method of the invention, by at most 15%, preferably at most 10%, most preferably at most 5%.

It is very well possible to perform the different steps at different temperatures, but each of the steps is performed at a maximum of 68° C.

It is to be noted that in order to bring the gelatin in solution, the medium can be heated to above 68° C., but such a step precedes the claimed method. But preferably, the gelatin is provided as an aqueous solution, where the aqueous solvent, in particular water, has not been heated to above 68° C., and not be heated to above the temperatures as described herein in order not to lose functionality.

To the said medium, a micelle-forming surfactant is added, as a result of which LPS is monomerised and said monomers are believed to interact with the surfactant, forming micelle complexes of surfactant and LPS.

Micelle-forming surfactants are known in the art, and are e.g. described in WO2009/15440, the contents of which are herewith incorporated herein. A micelle-forming surfactant is capable of forming micelles (soluble aggregates) in solution. To this end, the so-called critical micelle concentration (CMC) is defined as the concentration of surfactants above which micelles form and all additional surfactants added to the system go to micelles. At the CMC there is equilibrium with surfactant present on interfaces and the surfactant in the micellar state. The said CMC is temperature dependent; for non-ionic surfactants the CMC values increase on lowering the temperature (M. J. Schick J. Phys. Chem., 1963, 67 (9) 1796-1799). Further, elevation of temperature results in loss of solubility of the surfactant, the surfactant being present almost exclusively as insoluble aggregates, resulting in the solution becoming opaque or turbid. The temperature at which this takes place is the so-called cloud point. Increase of salt concentration results in lowering of the cloud point. For example the cloud point of a 1 w/w % TRITON X-100 solution decreases from 68° C. to room temperature by addition of 9-23% of $(NH_4)_2SO_4$ or 16%-25% (i.e. 2.74-4.27M) of NaCl, (Arnold and Linke, BioTechniques, 43 (2007), 427-440). Also, alcohols can be used to lower the cloud point (Gu and Galera-Gómez; Colloids and Surfaces A: Physicochemical and Engineering Aspects 147 (1999) 365-370).

Accordingly, herein, the term "cloud point" intends to indicate the temperature at which the surfactant forms insoluble aggregates in the medium. Said temperature depends on the conditions of the medium, such as salt concentration. When no specific conditions are given, the cloud point is defined herein as the temperature where a 1 w/w % aqueous solution forms insoluble aggregates. So, if the temperature is described to be below the cloud point of a surfactant, said temperature is 68-69° C. (i.e. for a 1 w/w % TRITON X-100 solution), but in case of a 16-25 w/w % NaCl solution, said cloud point is room temperature. As according to the invention it is important for the method that the temperature of the method steps stay below the cloud point i.e, the temperature should be such that the surfactant does not result in turbidity or opaqueness of the solution.

The cloud point can conveniently be determined under the given circumstances, by determining the light absorbance of the solution at 620 nm without addition of the surfactant, and check whether the absorbance increases when the envisaged amount of surfactant is added. Above the cloud point, the absorbance is increased. The determination of the absorbance can be performed according to the protocol of chapter 2.4.5 of the GME2014 (p. 96-99).

It was surprisingly found that elevation of the temperature above the cloud point is not necessary. Even more surprisingly, steps 1)-5) are more efficient when performed at temperatures below the cloud point of the micelle forming surfactant.

For the invention, it is sufficient for the surfactant to form micelles, i.e. soluble aggregates, without the need to form insoluble aggregates at elevated temperatures as explained above.

For efficient LPS removal, the micelle-forming surfactant is preferably present in a concentration of equal or above the CMC, so that soluble aggregates are formed that can be bound to the adsorbent. For TRITON X-100, the CMC is 0.015 w/w %.

While mixed aggregates of both LPS and surfactant are in solution, i.e. without the need of insoluble aggregates to be formed, the medium is contacted with a solid adsorbent, capable of binding the soluble aggregates of surfactant and LPS and monomers thereof. This can be done by adding particulate adsorbent to the medium, or by e.g. passing the medium through a filter element comprising the said adsorbent, or to incubate the medium with a carrier having the adsorbent present on the outer surface thereof. The skilled person is aware of suitable ways to bring an aqueous medium in contact with a solid adsorbent and to separate the adsorbent from the medium. The said separation can e.g. comprise centrifugation or filtration in case the adsorbent is added as a particulate to the medium, where filtration is preferred in view of industrial applicability. In a preferred embodiment, the adsorbent can be present in a filter, and the medium is passed through the said filter, or through a series of such filters, while the filters can optionally be washed in order to optimize the yield of the filtrate. This way, steps 3), 4) and 5) as described above can be combined in a single filtration step. Alternatively, larger bodies, such as rods, or beads, coated with the adsorbent can be soaked in the said medium, allowing binding of the LPS-surfactant complexes to the adsorbent, and can be removed from the medium thereafter. The adsorbent can also be stacked in a column, and the gelatin solution can pass over the column to remove surfactant and LPS.

At least steps 2) and 3), i.e. the step of adding the surfactant and the step of contacting with the adsorbant, but preferably all steps 1)-5) are performed at a temperature of at least 30° C., i.e. above the melting temperature of the gelatin. It is advantageous that the aqueous medium is a free flowing solution, i.e. having a measurable dynamic viscosity value (I.e. having a G" dominating behavior). Although the viscosity and gelling temperature varies for different gelatins, gelatin solutions are free flowing and well processable at a temperature of at least 30° C. A free flowing solution is advantageous when brought in contact with the adsorbent to allow for optimal contact between the medium and the adsorbent, and to secure proper separation of the adsorbent from the medium.

The aqueous medium is recovered and, if desired, the LPS count can be determined using, e.g. the LAL assay as described above.

The average molecular weight of the gelatin is preferably within the range of 1500 Da to 250 kDa, or even higher such as 300 kDa or 275 kDa, and any value within this range can be taken as upper or lower limit for defining a smaller range, such as e.g. a lower limit of 2000 Da, 4000 Da, 5000 Da, 15 kDa or 20 kDa, and an upper limit of e.g. 200 kDa, 180 kDa or 170 kDa. In case gelatin of e.g. medium or high bloom value is envisaged, the average molecular weight is above 120 kDa. In case gelatin hydrolysate is envisaged, the average molecular weight may be less than 70 or 80 kDa.

Although the micelle-forming surfactant can be an ionic surfactant, such as a cationic or anionic surfactant, the surfactant is preferably a non-ionic surfactant as such a surfactant tends to form micelles at lower concentration as compared to ionic surfactants. Further, ionic surfactants may interact with the gelatin by ionic bonds, and are more difficult to remove. Preferably, the micelle-forming non-ionic surfactant is an ethoxylated surfactant, preferably an alkylphenol ethoxylate, the alkylphenol ethoxylate preferably being represented by the formula $C_xH_{2x-1}-C_6H_4-O-(C_2H_4O)_nH$, wherein x is 4-12 and n is 7.5-14, X preferably being 8 and n preferably being 8-13, more preferably 8.5-12.5, most preferably 9-12, in particular TRITON X-100, TRITON X-102 (

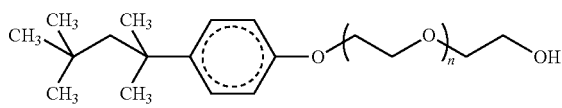

whereby n=on average 12.5), or mixtures thereof. It has been found that attractive results are obtained with TRITON X-100 and TRITON X-102. Although a higher value for n would result in a surfactant with higher solubility and higher cloud point, such longer surfactants appear to be less effective for LPS removal. However, other non-ionic surfactants that are suitable comprise nonylphenoxypolyethoxyethanols $C_{15}H_{24}O(C_2H_4O)_n$, n being 3-40, such as nonoxynol-4, nonoxynol-15 and nonoxynol-30, or polyethylene glycol sorbitan monoesters of $C_{12}$-$C_{18}$ fatty acids, such as TWEEN. CHAPSO (3-([3-cholamidopropyl]dimethyl ammonio)-2-hydroxyl-1-propanesulfonate) is another suitable non-ionic surfactant.

The solid adsorbent can be any suitable adsorbent, capable of binding the surfactant, and preferably also LPS, known to the skilled person, such as a hydrophobic adsorbent. The adsorbent is preferably insoluble, and suitable adsorbents comprises clays, such as (activated) diatomaceous earth or clays, phyllosilicates, such as aluminium phyllosilicate, smectite minerals and hydrophobic adsorbents, such as activated carbon, for example Norit SX Plus or Norit ROX 0.8 (Cabot, the Netherlands), or 3M ZetaCarbon filter cartridges, e.g. such as of the type R55S or R30L3S (3M, USA). Also mixtures of one or more adsorbents can be applied. The solid adsorbent can e.g. be added to gelatin containing aqueous medium and, after allowing the surfactant and preferably also the LPS to bind to the adsorbent, the adsorbent can be removed e.g. by filtration, sedimentation or centrifugation and the like. The contacting step is performed for a sufficient time to allow proper adsorption of the surfactant, resulting in removal of both the surfactant and the LPS bound to the surfactant and optionally also to the adsorbent. Preferably, the adsorbent is contacted with the aqueous medium for 5 minutes to 1 hour, more preferably for 10-30 minutes. A longer time period is possible, but less desired in view of process efficiency and a higher risk of gelatin hydrolysis in particular in case temperatures of above 60° C. or 65° C. are used. Shorter periods than 5 minutes are possible, but one may need to use more of the adsorbent as compared to incubation for a longer time period in order to arrive at the desired surfactant removal. In an attractive embodiment, the adsorption step can be repeated at least once, by contacting the recovered medium of step 5 again with solid adsorbent in a similar way as performed in step 2).

Preferably, each of the steps 1)-5) are performed at a temperature of 65° C. or less, more preferably 62° C. or less, even more preferably of 60° C. or less. As indicated above, elevation of the temperature to above 68° C. is not necessary to obtain efficient adsorption of surfactant and removal of LPS from the aqueous medium. It has also been surprisingly found that efficient removal of surfactant is obtained at even lower temperatures of 65° C., 62° C., 60° C., 58° C. or 55° C. The different steps can also be performed at different temperatures, but within the range of 30° C.-68° C. and above the cloud point of the surfactant used. In view of maintenance of functionality of the gelatin, the preferred temperature is between 55 and 65° C., such as 57° C.-60° C., or 58° C.

At least steps 2) and 3), but preferably all steps 1)-5) are preferably performed at a temperature of at least 35° C., more preferably of at least 40° C., even more preferably of at least 45° C., of at least 50° C., most preferably of at least 55° C. The gelatin solution is more liquid, i.e. less viscous at higher temperatures, which increases the handling of the solution and the contact with the adsorbant.

The pH of the medium is preferably between 3.5 and 9.0, more preferably between 3.5 and 8.0, 4.0 and 8.0, 4.0 and 6.0, even more preferably between 4.5 and 5.5. Below a pH of 3.5-4, the gelatin becomes susceptible for hydrolysis, in particular at temperatures above the melting point of the gelatin. The pH of the medium is therefore preferably above these pH values.

The skilled person knows that gelatin can be incubated or kept at a low pH without significant losing its functionality, but that this depends on the temperature and incubation time. The lower the pH, the lower the temperature should be, and/or the lower the incubation time in order not to lose functionality. The skilled person will however be able to determine proper conditions regarding pH, time and temperature to avoid hydrolysis of the gelatin. Very surprisingly, it has been found that when the method is performed at a low pH, the LPS is removed even more efficiently. Of course, care has to be taken to avoid hydrolysis of the gelatin when preforming the method at low pH, i.e. by performing the method at a moderate temperature not exceeding e.g. 58° C., 60° C. or 65° C. To this end, the pH of the aqueous medium comprising the gelatin is preferably between 4.0 and 6.0 throughout the method steps, more preferably between 4.5 and 5.5. At such pH, the temperature preferably is about 57-58° C. The total time wherein the medium is at such low pH during the method is preferably 2 hours or less, more preferably 1 hour or less, and even more preferably half hour or less.

The aqueous medium in step 1) may comprise any gelatin concentration. In a preferred embodiment, the aqueous medium in step 1) comprises at least 2 w/w %, preferably at least 8 w/w % and more preferably at least 12 w/w % dissolved gelatin and even more preferably at least 20 w/w % gelatin. The aqueous medium may comprise up to 30 w/w % dissolved gelatin or even higher, such as 37 w/w %, depending on the size of the gelatin molecules. An aqueous medium with a low gelatin concentration will have a lower gelling temperature than medium having a high gelatin concentration, allowing to perform the method at a lower temperature, which may be advantageous in case the incubation is to be performed at a low pH. Above 30-37%, the aqueous medium may become too viscous for proper processing, in particular for contacting and removal of the adsorbent. Only in case relatively small sized gelatin is used, such as gelatin hydrolysate, the concentration can be increased to about 40 w/w %. Elevation of the temperature to reduce the viscosity of such highly concentrated gelatin solutions can result in undesired gelatin hydrolysis and loss in molecular weight, viscosity and bloom value.

In step 2), the weight ratio of gelatin to added non-ionic surfactant is preferably 2000:1 or less, more preferably 500:1 or less, even more preferably 250:1 or less, most preferably 50:1 or less. The weight ratio of gelatin to added non-ionic surfactant is preferably 50-5:1. At higher weight ratios, i.e. where there is relatively more gelatin, not all LPS will be bound by the surfactant. On the other end, at lower ratios, the yield of gelatin may be imparted, or absorption is suboptimal at high levels of surfactant. In such a case, more rounds of adsorption may be needed for optimal surfactant removal. However, as LPS tends to bind stronger to the adsorbent, in particular in case of active carbon, it is usually chosen to use an excess of adsorbent as compared to surfactant in order to remove as much as surfactant as possible in a single step.

In step 2) of the method, the surfactant is preferably added to a concentration of 0.015-1.0 w/w %, more preferably of 0.020-0.50 w/w %, allowing proper removal thereof after having bound the LPS in the medium, still allowing a high gelatin content for efficient process-ability. The proper concentration of surfactant can also be adjusted to the LPS content in the gelatin. If the starting gelatin material has already a relatively low LPS content, a relatively low concentration (not largely exceeding the CMC value) of surfactant may be needed, which makes removal of the surfactant easier.

Step 2) of the method preferably comprises incubating the medium for at least 1 minute after adding the surfactant, more preferably 2 minutes to 1 hour, even more preferably for 5-30 minutes, most preferably for 15-30 minutes, in order to allow a proper binding of the LPS to the surfactant. Too long incubation, particular above 60° C., will increase the risk of gelatin hydrolysis and functionality (bloom, viscosity) loss.

In order to provide optimal removal of the surfactant, and the LPS from the medium, steps 3) and 4) preferably comprise passing the medium obtained after step 2) through one or more filter elements comprising the solid adsorbent. Filter systems containing activated carbon, e.g. 3M ZetaCarbon cartridge filter type R55S or R30L3S (3M, USA) have proven very suitable. The gelatin can be further recovered from the filtrate if desired, e.g. by isolation. Such filtration step may already provide for recovery of the gelatin with reduced endotoxin content in envisaged form, i.e. without the need for further recovery steps. In that case, steps 3), 4) and 5) comprise passing the medium obtained after step 2) through one or more filter elements comprising the solid adsorbent.

In another embodiment, in step 3) of the method the solid adsorbent is preferably added to the medium in a weight ratio to the surfactant of at least 2.5:1, more preferably of at least 3.0:1, most preferably of at least 3.5:1. The solid adsorbent is preferably added to the medium in a concentration of 0.1-3 w/w %, preferably of 0.5-1 w/w %. In case filter elements or systems are used, it may be preferred to use similar amounts of adsorbent in the filter system.

The recovering step 5) preferably comprises filtration, separating the solid adsorbent from the medium. This embodiment is advantageous when the adsorbent material is mixed, e.g. as particulate material, in the aqueous medium comprising the gelatin and the surfactant. As indicated above, the adsorbent can, although less preferred, also be centrifuged, or be bound to a carrier or the like. As indicated above, the filtration step can also be combined with step 3) and 4) by using filter elements comprising the adsorbent material.

According to the present invention, it is possible to work at low salt conditions, as the presence of salt is not necessary to carry out the invention. Although it is possible to include salt, e.g. to lower the cloud point of an envisaged surfactant for use in the method of the invention, this is not a necessary. In contrast, the conditions of the method steps are to be performed below the cloud point of the surfactant used, so there is no need to lower the cloud point. Furthermore, high salt concentrations, necessary to have an effect on the cloud point of the surfactant, are not preferred in the final purified gelatin and can affect the functionality thereof.

Therefore, in an attractive embodiment of the invention, the aqueous medium has a salt content 100 mM or less, preferably of 80, 70, 60 or 50 mM or less, most preferably of 40, 30 or 20 mM or less during steps 1)-5). Accordingly, it is possible to provide a gelatin solution having low endotoxin content with low salt content, without the need to include any desalting step. To this end, the recovered medium of step 5) preferably has a salt content of 100 mM or less, more preferably 80, 70, 60 or 50 mM or less, most preferably of 40, 30 or 20 mM or less.

As the method of the invention results in gelatin having low endotoxin content without the need of a centrifugation step, the method of the invention is preferably free of a centrifugation step. Such centrifugation step makes large scale recovery of gelatin with low endotoxin content difficult and costly. As the method of the invention can provide low endotoxin gelatin e.g. by filtration, a centrifugation step is preferably avoided.

As the method of the invention results in gelatin having low endotoxin content without the need of a laborious ultrafiltration step, the method of the invention is preferably free of an ultrafiltration step. This is not only advantageous in view of cost effectiveness, but it is also possible to obtain large sized, e.g. high bloom gelatin having an average molecular weight of 100 kDa or higher, such as 150 kDa or 200 kDa or 250 kDa or higher, which gelatins would not pass the ultrafiltration membrane.

Further, the yield is significantly less when using ultrafiltration. In another embodiment, the aqueous solution is substantially free of acetone, preferably of any ketone during steps 1)-5). In contrast to methods known in the art, the method of the present invention does not require addition of any ketone, which is in fact an undesired contaminant. In another embodiment, the aqueous solution is substantially free of alcohol, in particular ethanol.

In a particular embodiment, the method further comprises incubating the aqueous medium, with an oxidizing agent. It has surprisingly been found that the LPS content can be further reduced when an oxidizing agent is added to the medium during the claimed method, in particular during any of step 1), 2) or 3), preferably during step 2).

The oxidizing agent is preferably chosen from hydrogen peroxide and peracetic acid and mixtures thereof. Hydrogen peroxide is most preferred.

The oxidizing agent is preferably added in a concentration of 0.5-2.5 w/w %.

In the claimed method, the aqueous medium in step 1) preferably has a lipopolysaccharide content of 1000 EU/g dry weight of gelatin or less. In case the LPS content is higher, the medium can be pretreated e.g. by an ion exchange chromatography step, such e.g. is described for endotoxin removal from whole blood in EP0739630, or more in general by Hirayama and Sakata, supra. It is also possible to start with a gelatin preparation having a higher LPS content and perform the method of the invention by repeating steps 2)-5) with fresh materials in repeated steps 2) and 3). The aqueous medium of step 5) can then be used to provide the said medium in a new step if required.

If the starting material in step 1) has an LPS content of below 1500-1000 EU/g, a purified gelatin can be obtained in a single round of the 5 steps as described, comprising less than 100, less than 50, less than 20, less than 10, less than 5 or even less than 2 or even less than 1 EU lipopolysaccharide per gram gelatin (EU/g). The method according to the invention provides a purified gelatin in a single round of the 5 steps as described, comprising at least 50 times less LPS, preferably at least 100 times, more preferably at least 150 times, even more preferably at least 200 times and most preferably at least 250 times less LPS as compared to the LPS content in the starting material of step 1). The term EU is known in the art and reflects 'endotoxine units'. One EU is approximately equivalent to 100 pg of *E. coli* lipopolysaccharide, the amount present in about $10^4$-$10^5$ bacteria. Herein, the term EU/g reflects the EU count per dry weight of gelatin.

The invention also relates to gelatin, obtainable by the method of the invention, being substantially free of quaternary ammonium salts, comprising gelatin derived molecules having a molecular weight of above 100,000 Da, most preferably above 120,000 Da, having a lipopolysaccharide content of less than 100 EU/g, more preferably less than 50 EU/g, even more preferably less than 20 EU/g, even more preferably less than 10 EU/g, even more preferably less than 5 EU/g, even more preferably less than 2 EU/g, most preferably less than 1 EU/g. Not until the invention was made, it was possible to prepare such low endotoxin gelatin. Known ultrafiltration methods provide for gelatins wherein the gelatin molecules are not larger than 100,000 Da, so such gelatins do not comprise gelatin derived molecules having a molecular weight of above 100 kDa. Such gelatins are, at best, low bloom gelatins, or hydrolysates. Only by treatment with quaternary ammonium salts at high concentration, it has been shown possible to obtain low endotoxin gelatin of type B. However, the presence of salt may have an impact on the functionality of the gelatin. However, the present invention also provides low endotoxin gelatin with high molecular weight without the need to use quaternary ammonium salts. The term "gelatin derived molecules" intend to encompass protein and peptide molecules that were part of the collagen matrix in the raw material, which was processed for the preparation of gelatin, as e.g. known in the art.

In another embodiment the invention provides gelatin obtainable by the method of the invention, having a lipopolysaccharide content of less than 2 EU/g, preferably less than 1 EU/g. Gelatins, e.g. of both type A and B, having such a low LPS content can be prepared by the present method, whereas methods in the art provide gelatins with a higher LPS content.

In a particular embodiment, the invention relates to gelatin of type A, i.e. having an isoelectrical point of above 7 preferably above 8, obtainable by the method of the invention, comprising gelatin derived molecules having a molecular weight of above 100,000 Da, most preferably above 120,000 Da, having a lipopolysaccharide content of less than 100 EU/g, more preferably less than 50 EU/g, even more preferably less than 20 EU/g, even more preferably less than 10 EU/g, even more preferably less than 5 EU/g, even more preferably less than 2 EU/g, most preferably less than 1 EU/g. In the art, the only type A gelatin with such low endotoxin content is prepared by ultrafiltration, resulting in gelatin molecules smaller than 100 kDa. The present invention however, for the first time provides type A gelatin comprising larger gelatin molecules while still being very low in endotoxin content.

The gelatin of the invention preferably has an average molecular weight of the of between 1500 Da and 250,000 Da, more preferably between 2000 and 200,000 Da, even more preferably between 5000 and 180,000 Da, most preferably between 20,000 Da and 170,000 Da. The gelatin preferably has an average molecular weight of above 80,000 Da, preferably above 100,000 Da, most preferably above 120,000 Da.

In an attractive embodiment, the gelatin is free of acetone, preferably of any ketone. Further, the gelatin is preferably free of alcohol, in particular basic alcohols, and is preferably also free of quaternary ammonium salts.

In yet another embodiment, the invention relates to an aqueous medium comprising at least 2 w/w % gelatin of the invention, said medium having a salt content of 100 mM or less, preferably 50 mM or less, most preferably 20 mM or less. The aqueous medium is preferably substantially free of acetone and/or quaternary ammonium salts and/or alcohols, in particular basic alcohols. The aqueous medium preferably comprises at least 6 w/w %. preferably at least 10 w/w %, more preferably at least 15 w/w % and most preferably at least 20 w/w % gelatin.

The invention will now be further described by way of non-limiting examples and figures.

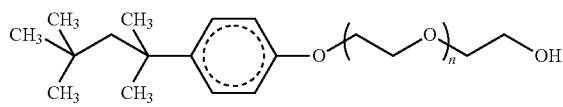

whereby n=on average 9.5) is found to be 0.015-0.018, equal to the said CMC in 25 water.

Figure 2:
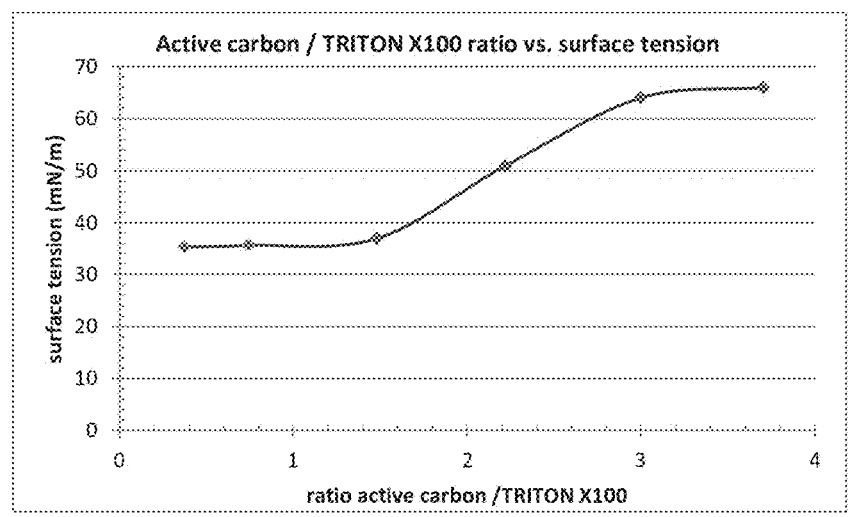

FIG. 2 is a graph, showing the surface tension of aqueous gelatin solutions as function of the ratio adsorbent to remove TRITON X-100 (

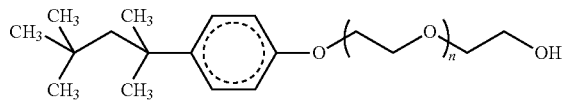

whereby n=on average 9.5) surfactant from the solution.

Figure 3:
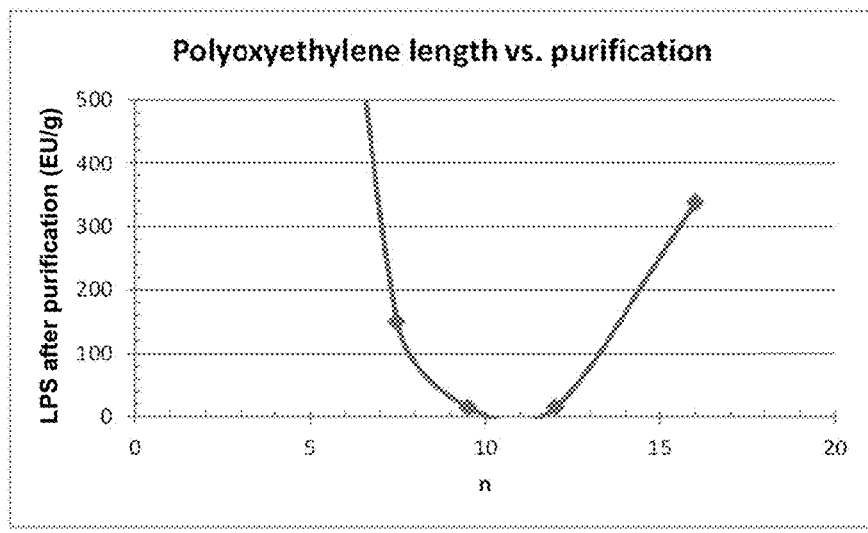

FIG. 3 is a graph, showing the effect of the length of the polyoxyethylene moiety in different Triton species used on the purification. The X axis represents the n number in the $C_8H_{15}$—$C_6H_4$—O—$(C_2H_4O)_n$H, and the Y axis shows the LPS content in EU/g in a gelatin containing LPS after purification.

EXAMPLES

A full overview of the gelatins used in the different examples is listed in table 1.

The analysis method to determine the gelatin properties is described in GME10.

In the examples, removal of surfactant was monitored, as surfactant, such as TRITON X100 can mask LAL analysis results. See example 4 for further details.

Unless indicated otherwise, mixing was performed with a speed of 750 rpm using a water-bath mixer from IKA Werke Germany, model R015 power and a standard magnetic stirrer bar of 4-5 cm length.

Unless otherwise indicated, the weight of gelatin indicated includes a moisture content of 10-13 w/w %.

Example 1

Endotoxin Purification from Aqueous Gelatin Solutions of Different LPS Content 6.66 w/w % gelatin solutions were prepared by weighing 50 g of the gelatin batches 1, 3, 4, 5, 6 and 8, 15, 16 and 17 with different initial LPS contents, varying from ~1000 to about 34,000 EU/g gelatin, (see table 1.1) with 700 ml water. The gelatins shown in Table 1 have a moisture content of between 10.3 and 12.6 w/w %. So the actual gelatin content on dry matter basis is 87.5-89.7%.

The mixture was kept at ambient temperature for 30 minutes to allow the gelatin to swell/hydrate. Subsequently, the gelatin was brought in solution by elevation of the temperature to a maximum of 60° C. under constant mixing for 30-45 minutes with a with a speed of 750 rpm. The pH of the gelatin solution was measured to be between 5.2 and 5.6, no further adjustment of pH was made. A sample was taken and the initial LPS content was measured. The Endosafe LAL method, from Charles River USA and the EndoZyme recombinant factor C method from Hyglos GmbH (Germany) were both used to analyse the LPS levels in the gelatins before and after purification.

Both methods were used according to the instructions of the manufacturer to determine the LPS content.

For the LPS analysis 1000 mg gelatin was dissolved in 40.0 ml deionized pyrogen free water. The gelatin was completely dissolved by heating the solution to 55° C. for 30-45 minutes, adjusted to 40° C. and appropriately diluted before the LPS analysis was executed.

Next, 1.4 g (0.18 w/w %) TRITON X100 (Carl-Roth, Germany, product number 3051.4) was added to the gelatin solution and the gelatin—TRITON X100 solution was, under constant mixing with a speed of 750 rpm, placed at 75° C. for 30 minutes.

TABLE 1.1

Gelatin starting materials

| Gelatin Batch number | Process and raw material | Endotoxin EU/g | bloom g | viscosity mPas | Mw kDa | pH | IEP | Cond. µS/cm | Moisture % | Production location** |
|---|---|---|---|---|---|---|---|---|---|---|
| 1 | Type A pigskin | 1000-1100 | 311 | 4.4 | 130 | 5.79 | 8.65 | 95 | 10.7 | G |
| 2 | Type A pigskin | 2800-3400 | 329 | 4.9 | 146.2 | 5.5 | 8.7 | 112 | 11.6 | G |
| 3 | Type A pigskin | 4900-5100 | 302 | 4.22 | 133 | 5.44 | 8.76 | 115 | 11.9 | G |
| 4 | Type A pigskin | 4100-4200 | 305 | 4.16 | 129.3 | 5.47 | 8.58 | 81 | 12 | G |
| 5 | Type A pigskin | 5000-5200 | 220 | 4.23 | 75.1 | 5.62 | 8.57 | 179 | 11.3 | G |
| 6 | Type A pigskin | 2400-2500 | 306 | 4.12 | 128.4 | 5.28 | 8.65 | 134 | 11.7 | G |
| 7 | Type A pigskin | 2800-3000 | 270 | 5.83 | 169 | 4.73 | 8.65 | 225 | 11.9 | A |
| 8 | Type A pigskin | 2800-3000 | 316 | 5.2 | 149.1 | 5.56 | 8.71 | 126 | 10.9 | G |
| 9 | Type A pigskin | 6800 | 53 | 1.6 | 50.5 | 5.23 | 7.64 | 185 | 12.6 | G |

TABLE 1.1-continued

Gelatin starting materials

| Gelatin Batch number | Process and raw material | Endotoxin EU/g | bloom g | viscosity mPas | Mw kDa | pH | IEP | Cond. µS/cm | Moisture % | Production location** |
|---|---|---|---|---|---|---|---|---|---|---|
| 10 | Type A pigskin | 17000-18000 | 0 | 5.0* | 4.9 | 5.2 | 7.5 | 434 | 7.5 | A |
| 11 | Type A fish | 32000-34000 | 275 | 3.55 | 104.3 | 6 | 8.6 | 108 | 12.2 | A |
| 12 | Type B bovine bone | 2900-3200 | 264 | 5.32 | 151.2 | 5.72 | 5.06 | 113 | 10.4 | P |
| 13 | Type B bovine bone | 6700-6800 | 254 | 5.38 | 153.1 | 5.74 | 4.86 | 102 | 10.3 | P |
| 14 | Type B bovine bone | 200-300 | 263 | 4.08 | 123 | 5.74 | 5.05 | 127 | 11.1 | I |
| 15 | Type A pigskin | 370-465 | 300 | 4.9 | 145.0 | 5.40 | 8.8 | 118 | 11.0 | G |
| 16 | Type A pigskin | 11000-12000 | 150 | 1.8 | 72 | 5.50 | 8.7 | 133 | 10.1 | A |
| 17 | Type A pigskin | 10000-11000 | 150 | 2.2 | 78 | 5.15 | 8.7 | 155 | 11.7 | G |

*viscosity was measured according to GME10, however, instead of a 6.67 w/w % solution, a 20 w/w % solution was used at 25° C.
**G: Rousselot bvba, Gent, Belgium; A: Rousselot AS, Angouleme, France; P: Rousselot Inc., Peabody, USA; I: Rousselot SASlaI, Isle sur la Sorgue, France Subsequently, a minimum of 5.0 g active carbon (Norit SX-Plus, Cabot, the Netherlands) was added (0.7 w/w %), followed by an additional 30 minutes mixing (500-1000 rpm) at 60° C. Next, the solution was filtered over a 0.45 µm filter (Phenex RC 26 mm, 0.45 µm (Phenomenex, The Netherlands) to remove active carbon and cooled to 40° C. for direct LPS analysis on the purified solution, or frozen at −20° C. and freeze dried using a Christ Alpha 2-4LD Plus freeze-dryer (MartinChrist, Germany). Freeze-drying vacuum conditions: 0.04 mbar and −87° C. for at least 24-48 hours until the solutions are dried to a moisture content of around 4-6%. No moisture correction was done before endotoxin analysis.

Filtration of an initial (non-purified) gelatin solution over a Phenex 0.45 µm filter did not influence or reduce the initial LPS level in the gelatin.

It can be observed from the data from table 1.2 that a very efficient LPS removal can be obtained from the starting materials. In order to obtain gelatins with an endotoxin content as low as 2 EU/g or less, it is preferred to start with a gelatin solution having 1500 EU/g endotoxin or less.

TABLE 1.2

LPS reduction in different gelatin batches

| Gelatins | Initial LPS level (EU/g) | Purified LPS level (EU/g) | Purification factor |
|---|---|---|---|
| Gelatin 1 | 1100 | 1 | 1100 |
| Gelatin 3 | 4960 | 190 | 26 |
| Gelatin 4 | 4200 | 142 | 30 |
| Gelatin 5 | 5120 | 28 | 182 |
| Gelatin 6 | 2480 | 109 | 23 |
| Gelatin 8 | 2912 | 39 | 75 |
| Gelatin 15 | 372 | 1 | 372 |
| Gelatin 15 | 465 | 2 | 232 |
| Gelatin 16 | 11467 | 7 | 1638 |
| Gelatin 17 | 10728 | 9 | 1192 |

Example 2

Variation of Surfactant Concentration

Three 6.66% w/w gelatin solutions were prepared as described for example 1, using the gelatin batches 1, 2 and 15, having almost similar average molecular weight and viscosity, see table 1. Different amounts of TRITON X100 (Carl-Roth, product number 3051.4) were added to the solution (see table 3) followed by mixing at maximum 60° C. for 30 minutes. Subsequently, 5.0 g (0.7 w/w %) active carbon (Norit SX-Plus) was added to tests 2-3-4-5. Followed by mixing at maximum 60° C. for 30 minutes at 500-1000 rpm and removed as described in example 1, using a 0.45 µm filter (Phenex RC 26 mm, 0.45 µm). The Active carbon amounts was increased for test 6 to respectively 20 g to assure that all TRITON X100 will be removed from the purified gelatin solution. Surface tension analysis confirmed indeed that the TRITON X100 concentration were reduce to value below the CMC.

After purification the gelatins were stored at −20° C. and freeze-dried as described in example 1. The freeze-dried gelatins were used for the LAL LPS analysis.

Table 2 indicates that a TRITON concententration of above the CMC thereof is shown to be advantageous for endotoxin removal.

TABLE 2

LPS reduction on different levels of TRITON X

| Test | Triton x 100 g per 50 g gelatin | Conc. Triton X100 (w/w %) | LPS value (EU/g) Gelatin 1 | LPS value (EU/g) Gelatin 2 | LPS value (EU/g) Gelatin 15 |
|---|---|---|---|---|---|
| 1 | 0 | 0 | 1100 | 5400 | 442 |
| 2 | 0.048 | 0.0065 | 1000 | 3800 | |
| 3 | 0.097 | 0.014 | 100 | 450 | |
| 4 | 0.194 | 0.026 | 16 | 38 | |
| 5 | 1.36 | 0.18 | 1-10 | 16 | 1 |
| 6 | 7.95 | 1.05 | <1 | 15 | 1 |

Example 3

Diatomaceous Earth as LPS Purification Agent 600 ml 6.66 w/w % gelatine 1 and 9 solution was prepared at pH 5.5, and treated with TRITON X100 as described in example 1. After the incubation step of 30 minutes at a maximum temperature of 60° C., instead of active carbon, 70 gram diatomaceous earth (Claracel CBL), pre-washed with deionized water, was added followed by 4 hours continuous mixing at 50° C. After 4 hours, the diatomaceous earth was removed by filtration (Whatman Glass microfiber GF/C grade, 55 mm diameter, 2 mm. Schleicher & Schuell, Germany). The filtered gelatin solution was overnight stored at −20° C., followed by freeze-drying (see example 1 for the freeze-drying conditions). A non-purified 6.67% gelatin 1 and 9 sample were also stored at −20% and freeze-dried. The LPS content was analyzed on the purified and non-purified freeze-dried gelatin samples, see table 3.

A significant amount of the endotoxin can be removed from the gelatin using diatomaceous earth as adsorbent. The LPS purification is however somewhat less efficient as compared to that when active carbon is used, see gelatin 1. However, it is also possible to apply diatomaceous earth in a pre-purification step.

TABLE 3

LPS reduction with diatomaceous earth as adsorbent

| Gelatins | Initial LPS level (EU/g) | Purified LPS level (EU/g) | Purification factor |
|---|---|---|---|
| Gelatin 1 | 1036 | 39 | 26 |
| Gelatin 9 | 6800 | 300 | 23 |

Example 4

Variation of Amount of Adsorbent

Figure 1:
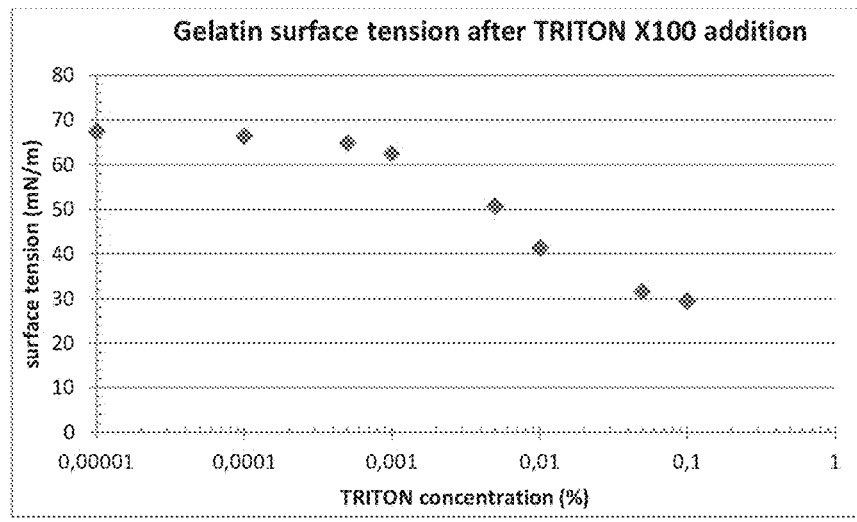
FIG. 1 is a graph, shows the effect of surfactant concentration on the surface tension of an aqueous gelation solution at 25° C. The CMC of TRITON X-100 (

The efficiency of removal of surfactant by the adsorbent is analyzed by measuring the surface tension of the samples before addition of the surfactant to the medium comprising the gelatin, and compared with the surface tension measured after treatment with adsorbent and removal thereof. Surface tension drops in the presence of surfactant, e.g. TRITON X100. FIG. 1 shows that the initial surface tension of a 1 w/w % gelatin solution of 65-67 mN/m drops significantly starting at a TRITON concentration of 0.001 w/w %, based on the weight of the solution. The critical micelle concentration of TRITON X100 is between 0.014 and 0.018% w/w.

Surface tension was analyzed using the Digidrop (GBX, France) contact angle/surface tension analysis equipment. The needle diameter was 0.81 mm and the drop formation speed was 0.384 µl/s. Maximum drop volume is 9.900 µl. Surface tension was calculated using the ds/de equation.

In case high amounts of surfactant are used, a corresponding higher amount of adsorbent may be needed to remove the said surfactant from the solution. It is also possible to repeat the adsorption step in order to remove any residual surfactant, not removed in a first round of adsorption, until a surface tension value of 65-67 mN/m equal to pure gelatin is obtained.

Solutions of 50, 60 and 100 g gelatin 7 (see table 1) in 700 ml water were prepared as described in example 1, resulting in gelatin concentrations of 6.66, 8.0 and 12.5 w/w %, respectively. TRITON X100 (Carl-Roth) amounts added were 1.4 g (0.18 w/w %) for a 6.67% gelatin solution, 1.7 g (0.216 w/w % for a 8% gelatin solution and 2.8 g (0.36 w/w %) for a 12.5% gelatin solution. Mixing was done at a speed of 500-1000 rpm at 60° C.

The active carbon (Norit SX-Plus) amounts added were varied and also increased in line with the TRITON X100 concentration increase, see table 4. After active carbon addition the mixture was mixed for an additional 30 minutes at 60° C. at a speed of 500-1000 rpm. Finally the solutions were filtered equally to example 1 using 0.45 µm filter (Phenex RC 26 mm, 0.45 µm). The filtered solutions were used to measure the surface tension, see table 4. It can be observed from table 4 and FIG. 2 that at a weight ratio active carbon:TRITON X100 of 2.5 or higher results in a surface tension close to the initial gelatin solution without added surfactant. At a weight ratio of 3 or higher, in particular of 3.5 or higher, the surface tension are equal to that of the initial gelatin solution, indicating that the surfactant has been removed substantially completely. A higher (above 3.5) active carbon:TRITON ratio results in an even more efficient TRITON X100 reduction. See also FIG. 2.

TABLE 4

Active carbon/Triton ratio and effect on surface tension

| Active carbon | Triton X100 g (w/w % in solution) | Gelatin g (w/w % in solution) | Ratio active carbon: Triton X100 | Surface Tension (mN/m) |
|---|---|---|---|---|
| — | — | 100 g (12.5) | — | 66.1 |
| 5 g | 1.35 g (0.18) | 50 g (6.7) | 3.7 | 65.8/66.0 |
| 6 g | 2.0 g (0.26) | 60 g (8) | 3.0 | 65.0 |
| 8 g | 2.7 g (0.34) | 100 g (12.5) | 3.0 | 64.5/66.5 |
| 1 g | 2.7 g (0.34) | 100 g (12.5) | 0.37 | 35.36 |
| 2 g | 2.7 g (0.34) | 100 g (12.5) | 0.74 | 35.7 |
| 4 g | 2.7 g (0.34) | 100 g (12.5) | 1.48 | 36.98 |
| 6 g | 2.7 g (0.34) | 100 g (12.5) | 2.22 | 51 |
| 8 g | 2.7 g (0.34) | 100 g (12.5) | 3 | 64 |
| 8 g | 2.8 g (0.35) | 100 g (12.5) | 2.9 | 66.0 |
| 10 g | 2.7 g (0.34) | 100 g (12.5) | 3.7 | 66 |

Example 5

Temperature Variation, Influence on LPS Removal and Functionality.

A same test as described in example 2 was performed on gelatin 1. pH adjustment was done to a value of 5.5. After TRITON X100 addition, the solution was mixed at 60° C. for 15 minutes, and subsequently, the temperature was adjusted to the temperatures listed in table 5 followed by an additional maximum 30 minutes mixing at 500-1000 rpm. Two different TRITON X100 concentrations were used, 0.18 and 0.026 w/w %.

Subsequently, treatment with active carbon and solution filtration was performed according to example 1. In addition to LPS analysis, also analysis of the viscosity of the solutions as well as the average molecular weight of the gelatin were performed as an indication of functionality of the gelatin after treatment.

Viscosity was analyzed according to the method described in the GME10. Molecular weight distribution was measured according to Olijve et. al., supra.

Gelatins were freeze-dried before LPS analysis as described before.

TABLE 5

Temperature variation at pH 5.5 - gelatin 1

| | | | Triton X100 concentration (w/w %) | |
|---|---|---|---|---|
| Temperature (° C.) | Mw (kDa) | viscosity (mPas) | 0.18 Purified LPS level (EU/g)) | 0.026 Purified LPS level (EU/g) |
| non-treated | 130 | 4.4 | 1050 | 1050 |
| 57.5 | 129.5 | 4.4 | 2 | 6 |
| 65.0 | 127.5 | 4.3 | 5-6 | 6 |
| 80.0 | 110 | 4 | 8 | 11 |
| 90.0 | 46 | 0.8 | 10 | 20 |

It can clearly be observed that at a temperature of 90° C., the gelatin is hydrolyzed and loses its functionality. The viscosity decreases from an initial value of 4.4 to 0.8 mPas and the average molecular weight decreases from 130 to 46 kDa, i.e. a molecular weight loss of 65%. Also at a temperature of 80° C., the reduction in molecular weight and viscosity is significant as well. However, at temperatures of 65° C. or lower (below the cloud point of TRITON X100), where significant hydrolysis is prevented, functionality is maintained, and surprisingly, a very efficient LPS removal is observed, which is equal to, or at lower TRITON X100 concentration, even slightly better than at higher temperatures.

Example 6 pH and Temperature Variation, Influence on LPS Removal and Functionality

This example was performed as described in example 5. Gelatins 1, 2, 3, 7, 8 and 10 were used for the purification. In addition to the temperature, also pH of the purification solution was adjusted and varied. After addition of TRITON X100 (0.026 and 0.18 w/w %), the temperature was adjusted from 57.5 to 90° C. as indicated in table 6.1 and followed by 30 minutes mixing at 500-1000 rpm. Subsequently, 5.0 gram active carbon (Norit SX-Plus) was added and the solution was mixed for an additional 15-30 minutes at 500-1000 rpm. Next the solution was filtered using a 0.45 □m filter as described in the previous examples. Gelatins were freeze-dried before LPS analysis as described before. In table 6.1 temperature variation was executed with gelatin 7 with a pH adjustment to pH 4.5. Temperature will become much more critical in relation to gelatin hydrolysis at lower pH values. Besides the endotoxin (LPS) analysis also the molecular weight and viscosity values were measured after purification to observe possible gelatin hydrolysis and loss in gelatin properties. Viscosity and molecular weight distribution analysis was measured using the methods mentioned in example 5.

TABLE 6.1

Temperature variation at a pH of 4.5 - gelatin 7

| | | | Triton X100 concentration (%) | |
|---|---|---|---|---|
| temperature (° C.) | Mw (kDa | viscosity (mPas) | 0.18 Purified LPS level (EU/g) | 0.026 Purified LPS level (EU/g) |
| non-treated | 169 | 5.8 | 2900 | 2900 |
| 57.5 | 169.5 | 5.8 | 15 | 28 |
| 65 | 158.6 | 5.4 | 12 | 21 |
| 80 | 140.0 | 4.6 | 15 | 45 |
| 90 | 52.0 | 1.2 | 16 | 35 |

It is observed that a temperature above 65° C., in particular at 80 and 90° C., and a low pH of 4.5 leads to loss of molecular weight and viscosity under the test conditions used, see table 6.1. Therefore, the gelatin is preferably be held at 65° C. or lower during the steps of the method for 15 minutes or less. Most preferably, the temperature during the steps of the method do not exceed 60° C. if the pH is 4.5 or lower, such as 4.0.

To confirm the results of table 6.1 a wider pH range was tested using gelatin 2, 3 and 7 at temperatures of 57.5° C., i.e. below and above the temperature where gelatin hydrolyses (60° C.).

The pH ranges applied are listed in the table 6.2. The pH adjustment of the gelatin solution was done before the TRITON X100 addition with 0.1M hydrochloric acid (Sigma Aldrich, 258148-500ML) or 0.1M NaOH (Sigma-Aldrich, USA, 221465-500G). Instead of hydro-chloric acid also other acids, such as sulfuric acid (Sigma-Aldrich) can be used to lower the pH. It is to be observed that the chloride concentration after pH adjustment was below 50 mM, which concentration does not affect the cloud point of the surfactant used.

The gelatin solution preparation and the TRITON X100 (0.18 w/w %), active carbon addition (5 gram 0.7 w/w %), mixing and filtration of the gelatin samples was equal to the methods described in the previous examples. Gelatins were freeze-dried before LPS analysis as described before. The LPS purification results at 57.5° C. and the molecular weight and viscosity measured after purification are provided in table 6.2.

Variation of the pH at 57.5° C. did not result in phase separation of the micellar aqueous phase.

TABLE 6.2 pH variation at 57.5° C., Triton X100 0.18% (W/W)

| | Gelatin 2 | | | Gelatin 3 | | | Gelatin 7 | | |
|---|---|---|---|---|---|---|---|---|---|
| pH | Mw (kDa) | Viscosity (mPas) | Purified LPS (EU/g) | Mw (kDa) | Viscosity (mPas) | Purified LPS (EU/g) | Mw (kDa) | Viscosity (mPas) | Purified LPS (EU/g) |
| 3 | 109 | 3.7 | | 101.3 | 3.15 | | 127.7 | 4.2 | 14 |
| 4 | 130 | 4.4 | | 118.9 | 3.85 | | 151.6 | 5.2 | 15 |
| 4.5 | 139 | 4.7 | 10 | 129.7 | 4.15 | 20 | 167.5 | 5.8 | 15 |
| 5 | 142 | 4.8 | | 131.6 | 4.2 | | | | |
| 5.5 | 144 | 4.8 | 140 | 133.8 | 4.3 | 150 | 166.9 | 5.9 | 45 |
| 6 | 145 | 4.9 | | 134.6 | 4.3 | | 168.2 | 5.92 | 118 |
| 7 | 145.5 | 4.9 | | 134.8 | 4.3 | | 168.5 | 5.95 | 140 |
| Non-treated gelatin | 146.2 | 4.9 | | 135.1 | 4.22 | | 169.4 | 5.90 | 2850 |

Variation of pH at 57.5° C. results in limited loss in molecular weight and viscosity at pH values above 4.5, see table 6.2. Significant LPS purification without loss in molecular weight/viscosity is obtained between pH values of 4.5 and 5.6. In particular for gelatin 7.

Various gelatins (1, 2, 3, 7, 8, 10) were tested at a temperature of 57.5° C. at pH 4.5 and 5.5 to compare purification efficiency without loss in molecular weight and viscosity, table 6.3. The gelatin solution preparation was performed as described above. If required, the pH was adjusted to 4.5 and 5.5 with 0.1M hydrochloric acid (Sigma Aldrich, 258148-500ML) or 0.1M NaOH (Sigma-Aldrich, 221465-500G). Instead of hydrochloric acid also other acids such as sulfuric acid (Sigma-Aldrich) can be used.

The TRITON X100 concentration used was 0.18 w/w % and a minimum of 5 g active carbon was admixed. The gelatin solution was filtered before LPS analysis as described for the previous examples. Gelatins were freeze-dried before LPS analysis as described above.

An improved LPS purification is visible at pH values of 4.5 compared to 5.5. The influence of improved LPS purification at lower pH looks to be larger at higher initial LPS values. Lower pH is preferred in case low LPS levels (<20 EU/g) are required. No significant change in molecular weight distribution was observed between pH 4.5 and 5.5 for the tested gelatins at 57.5° C., values not listed.

TABLE 6.3

LPS removal at pH 4.5 and 5.5 at 57.5° C. for different gelatins

| Gelatins | Initial LPS (EU/g) | Purified LPS level (EU/g) at pH 5.5. | Purified LPS level (EU/g) at pH 4.5. |
|---|---|---|---|
| Gelatin 1 | 1050 | 2-7 | 2-5 |
| Gelatin 2 | 3400 | 140 | 10 |
| Gelatin 3 | 5040 | 150 | 20 |
| Gelatin 7 | 2850 | 45 | 15 |
| Gelatin 8 | 2950 | 33 | 15 |
| Gelatin 10 | 17640 | 288 | 55 |

Example 7

LPS Removal Above and Below the Cloud Point of the Surfactant

Purpose was to measure the LPS removal from gelatin solutions at conditions below the cloud point of the surfactant used, as compared to conditions above the cloud point. In order to keep the conditions similar, temperature conditions of 57.5° C. were used while using TRITON X-100 (cloud point of 68° C.) as well as TRITON X-114 (Sigma-Aldrich, cloud point of 23° C.) as surfactant.

Gelatin 7 was used to prepare a gelatin solution as described in the previous examples. The pH applied was 4.7. TRITON X-100, TRITON X-114 or mixtures thereof were used as surfactant in a concentration of 0.18 w/w %. After the surfactant was added to the aqueous gelatin medium, the temperature was adjusted to 57.5° C. followed by 15-30 minutes mixing. Active carbon was added to an amount of at least 5 gram (0.7 w/w %) and an additional mixing was done for 15-30 minutes. After filtration, as described in the previous experiments, the gelatins were freeze-dried before LPS analysis as described above.

Results are given in table 7. It can be seen that when using TRITON X-100 at a temperature above the cloud point thereof, i.e. at a temperature of 75° C., a gelatin solution is obtained that still contains 27 EU/g LPS, as compared to only 15 EU/g when the method was performed at 57.5° C., i.e. below the said cloud point. This means that LPS removal is more efficient when the method is performed below the cloud point of the surfactant. In addition, at 75° C., significant hydrolysis of gelatin occurs, resulting in undesired loss of viscosity and functionality, see e.g. example 6. At 75° C., the viscosity reduced from 5.8 mPas to about 4.9 mPas, whereas at 57.5° C., the viscosity remained 5.8 mPas. Using TRITON X-114 at 57.5° C. resulted in a gelatin solution still having 114 to 150 EU/g LPS, indicating that in comparison with TRITON X-100 at 75° C., i.e. both at conditions above the cloud point of the respective surfactant, TRITON X-100 results in better LPS removal. At the same temperature (at 57.5° C., i.e. below the cloud point of TRITON X-100 but above that of TRITON X-114) the difference in LPS removal is even more pronounced.

From a mixing experiment, it is clear that the more relative amount of TRITON X-100 as compared to the of TRITON X-114, the better the LPS removal is.

TABLE 7

Triton X114 an Triton X100 as surfactant

| Amount Triton X100 (%)* | Amount Triton X114 (%)* | LPS (EU/g) | Temperature (° C.) |
|---|---|---|---|
| 100 | 0 | 26.8 | >75 |
| 100 | 0 | 15.0 | <60 |
| 80 | 20 | 19.8 | <60 |
| 50 | 50 | 44.5 | <60 |
| 20 | 80 | 85.0 | <60 |
| 0 | 100 | 150-114 | <60 |

*Mix ratios of Triton X100 and Triton X114 to obtain a total of 0.18% w/w surfactant solution.
** 75° C. is above and <60° C. (i.e. 57.5° C.) is below the Triton X100 cloud point.

Example 8

Effect of Gelatin Concentration on LPS Removal.

A test as described in example 1 has been performed with gelatin 7 wherein the gelatin concentration varied from 6.66 w/w % to 10 w/w % and 15 w/w %, see table 8. The TRITON X100 concentration was increased in equal ratio to the gelatin concentration. For a 6.67% gelatin concentration 1.4 g (0.18 w/w %) TRITON X100 was applied. For a 10 w/w % gelatin solution 2.1 g (0.27 w/w %) and for a 15 w/w % gelatin solution 3.2 g (0.40 w/w %) TRITON X100 was used. In line with TRITON X100, also the active carbon amounts added were increased from 5 gram (0.7 w/w %) for the 6.66% gelatin solution to 7.5 gram (1.05 w/w %) and 11.3 gram (1.6 w/w %) for the 10 and 15% (w/w) gelatin solutions, respectively. Mixing during the various purification steps was done at 500-1000 rpm for 15-30 minutes. The gelatins were filtered using filtration over a 2 □m filter (Whatman® Glass microfiber filters GF/C grade, 55 mm diameter, 2 μm (Schleicher & Schuell), using a Buchner funnel. Gelatins were freeze-dried before LPS analysis as described before.

At higher gelatin concentrations, the filtration step to remove the activated carbon requires more efforts. To confirm possible remaining TRITON X100 traces which can influence the LPS/LAL analysis, surface tension measurements were performed as described in example 4 above. The surface tension results are equal/close to the original gelatin containing no TRITON X100.

TABLE 8

Effect of gelatin concentration on LPS removal, gelatin 7, pH 4.7 and 57.5° C.

| Gelatin concentration (%) | Purified LPS Level (EU/g) | Surface tension (mN/m) |
|---|---|---|
| 6.66 | 15 | 65.7 |
| 10 | 16 | 65.0 |
| 15 | 50 | 65.0 |
| Gelatin non treated | 2950 | 66.1 |

The LPS purification is hardly affected by gelatin concentration. Also at high, 15 w/w % gelatin solutions an effective purification was measured.

Example 9

Comparison of different TRITON.

6.66 w/w % gelatin solutions were prepared as described in example 1, using gelatin batch 5. 0.18 w/w % of different TRITON species were added to the gelatin solutions followed by mixing at 55° C. for 30 minutes. Subsequently, 5.0 g (0.7 w/w %) active carbon (Norit SX-Plus) was added, mixed at 55° C. for 30 minutes at 500-1000 rpm and removed as described in example 1, using a 0.45 µm filter (Phenex RC 26 mm, 0.45 µm). After purification the gelatins were stored at −20° C. and freeze-dried as described in example 1. Purified and non-purified liquid gelatin samples were stored at −20° C. and freeze-dried before LPS analysis.

It was observed that with TRITON species having the formula $C_8H_{15}$—$C_6H_4$—O—$(C_2H_4O)_nH$ wherein n is between 8 and 13, a low LPS content of 20 EU or less could be achieved. The purified gelatin had a molecular weight and a viscosity comparable to the initial gelatin before purification.

TABLE 9

LPS reduction with different Triton at 55° C.

| Triton | LPS level (EU/g) | N number |
|---|---|---|
| Triton X165 | 350 | 16 |
| Triton X102 | 15 | 12 |
| Triton X100 | 10 | 9.5 |
| Triton X114 | 150 | 7.5 |
| Non-treated gelatin 5 | 5200 | |

FIG. 3 shows a graph wherein TRITON X100, TRITON X102, TRITON X114 and TRITON X165 (

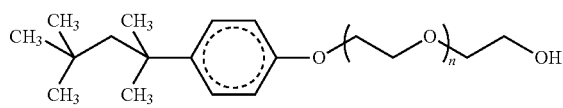

whereby n=on average 16) are used in the purification of gelatin. The graph shows that when the n value lies between 8 and 13, specifically between 8.5 and 12.5 a better purification is obtained of about 20 EU/g or less. It is noted that the use of both TRITON X-114 (n of 7.5) and TritonTRITON-X165 (n of 16) also resulted in reducing the level of the LPS content in a gelatin-containing LPS but not to the levels obtained with TRITONs having an "n" value between 8 and 13 such as TRITON X-100 and TRITON X-102.

Example 10

Purification of Type B Bone Gelatin.

The test conditions are equal to the previous described examples.

A 6.66% (w/w) gelatin 12, 13 and 14 solution was prepared and the temperature was kept at 57.5° C. pH of the gelatin solution was not adjusted. TRITON X100 was added to a concentration of 0.18 w/w % and mixed for 30 minutes. Subsequently, an amount of 5.0 g (0.7 w/w %) active carbon was added followed by an additional 15 minutes mixing. Finally the gelatin solutions was filtered as described before. Temperature was kept at 57.5° C. The LPS level of the filtered gelatin solution was measured directly or first frozen at −20° C. followed by freeze-drying as described in the previous examples.

The TRITON X100 purification method is also very effective to purify type B gelatins to levels below 20 EU/g. Lower purified LPS levels are obtained in case the LPS level in the starting gelatin is lower.

TABLE 10

Purification of Type B gelatin

| gelatin | pH | Initial LPS level (EU/g) | Purified LPS level (EU/g) |
|---|---|---|---|
| 12 | 5.7 | 3200 | 70 |
| 13 | 5.8 | 6720 | 20 |
| 14 | 5.4 | 250 | 8.4 |

Example 11

Purification of Type B Bone Gelatin at Different pH Values.

The conditions were equal to the conditions used in example 10. Gelatin 12 solution were prepared and pH was adjusted to values between 4 and 6 using either 0.1M hydro-chloric acid or 0.1M sodium hydroxide, both from Sigma-Aldrich. Gelatins were freeze-dried before LPS analysis as described above.

TABLE 11

Type B, gelatin 15, purification at different pH values at 57.5° C.

| Gelatin (12) | LPS content (EU/g) |
|---|---|
| Non purified, initial LPS value | 3200 |
| Purified at pH 4.0 | 44 |
| Purified at pH 4.5 | 44 |
| Purified at pH 5.0 | 44 |
| Purified at pH 6.0 | 71 |
| Purified at pH 7.0 | 78 |

A pH effect is observed. Particular at values below 6.0, improved LPS purification was observed.

Example 12

Purification of Type a Fish Gelatin.

The test conditions were as described for examples 10 and 11.

A 6.66% (w/w) gelatin 11 solution was prepared at 57.5° C. and TRITON X100 was added to a concentration of 0.18 w/w %. Subsequently, an amount of 5.0 g active carbon was added followed by an additional 15 minutes mixing. Finally the solution was filtered as described before. Temperature was kept at 57.5° C. The pH of the gelatin solution was not adjusted and was kept at 5.7. Gelatins were freeze-dried before LPS analysis as described before.

TABLE 12

Type A fish gelatin purification:

| Gelatin (11) | LPS content (EU/g) |
|---|---|
| Non purified | 33760 |
| LPS content after purification | 80 |

The TRITON X100 purification is very efficient to purify high LPS containing fish gelatin. It was observed that the level of purification for the type A fish gelatin can further be improved by decreasing the pH of the fish gelatin solution to values between 4.5 and 5.5. An additional purification by repetition of steps 2)-5) can be executed to obtain levels <20/<10/<5 EU/g, as result of the initial high LPS level.

Example 13

Different Active Carbon Removal Methods
A gelatin 7 solution was prepared as mentioned in the previous examples.
A TRITON X100 concentration 0.18 w/w % was applied. The solution was mixed for 30 minutes at 750 rpm at 57.5° C. Next, 5 gram (0.7 w/w %) active carbon was added followed by an additional 15-30 minutes mixing at 57.5° C. After incubation the active carbon was removed in three different ways:
 1. Filtration over a 0.45 μm filter, as described in previous examples
 2. Filtration over a 2 μm filter (Whatman® Glass microfiber filters GF/C grade, 55 mm diameter, 2 μm (Schleicher & Schuell), using a Buchner funnel. Larger filter pores are beneficial for processing.
 3. Filtration over non activated diatomaceous earth (Clarcel CBL, Ceca Chemicals, France, or Sigma-Aldrich D3877, Sigma-Aldrich, USA), using a Buchner funnel. 7.5-10 gram diatomaceous earth was used per 125 gram 6.67% gelatin solution containing 0.18 w/w % TRITON X100 and 0.7 w/w % active carbon. Diatomaceous earth is a well-known filtration aid, e.g. used in the gelatin production process.
Gelatins were freeze-dried before LPS analysis as described before.
The surface tension of the filtered gelatine solutions mentioned in table 13 was 66-67 mN/m, equal to the non-treated gelatin control solution (data not shown).
All 3 filtration methods can be used to effectively remove active carbon and the adsorbed TRITON X100 and LPS. The results suggest that filtration over diatomaceous earth is more effective compared to a 0.45 μm and a 2 μm filter and suggests an additional LPS purification by diatomaceous earth.

TABLE 13

Different active carbon removal methods

| Gelatin (7) | LPS content (EU/g) |
|---|---|
| Non-treated gelatin | 2850 |
| Purified, active carbon filtration according to method 1 | 34 |
| Purified, active carbon filtration according to method 2 | 17 |
| Purified, active carbon filtration with diatomaceous earth | 1.5 |

In another experiment, the active carbon was not introduced into the gelatin solution, but the aqueous medium comprising both gelatin and the surfactant were passed through a 3M ZetaCarbon filter cartridge of the R55S type (3M, USA), resulting in improved LPS removal as compared to the above method 2. Also, the surface tension of the solution after passing the filter was 66-67 mN/m, equal to the non-treated gelatin control solution, indicating that the surfactant substantially completely remained in the filter, see also example 4. In cases where the surface tension is not similar to the control solution, two or if desired more filter cartridges can be used in series. Similar results were found when instead of the R55S filter, a filter of the R30L3S type (3M, USA) was used.

Example 14

Effects of TRITON X100, Oxidation and Combined TRITON X100-Oxidation
Three different 6.66% gelatin 1 and gelatin 10 solutions were prepared according the methods described in example 1. To one solution TRITON X100 was added to a concentration of 0.18 w/w %. To the second solution, $H_2O_2$ was added to a concentration of 1.5 w/w %. To the third solution, TRITON X100 and $H_2O_2$ were added to the concentration of 0.18 w/w % and 1.5% w/w % respectively. pH of the solutions were not adjusted and were 5.5 and 5.3 for gelatin 1 and gelatin 10 respectively. Mixing and incubation was done at 57.5° C. for 30 minutes. A minimum of 5 gram (0.7 w/w %) active carbon was added to gelatin solutions followed by an additional 15-30 minutes mixing. Subsequently, the gelatin solutions were filtered using a 0.45 μm filter (Phenex RC 26 mm, 0.45 μm) as described in example 1. Gelatins were freeze-dried before LPS analysis as described above. Remaining $H_2O_2$ was analyzed using the method described in the GME10 and was <20 ppm, confirming that no interference with the LAL analysis method occurred.

TABLE 14

Oxidizing agents - Triton X100 effect with gelatin 1 and gelatin 10

| Treatment | LPS content (EU/g) |
|---|---|
| Gelatin 1 | |
| Initial | 1075 |
| Triton X100 | 2 |
| 1.5% $H_2O_2$ | 122 |
| Triton X100 + $H_2O_2$ | <1 |
| Gelatin 10 | |
| Initial | 17640 |
| Triton X100 | 288 |
| 1.5% $H_2O_2$ | 3116 |
| Triton X100 + $H_2O_2$ | 18 |

From Hirayama and Sakata, supra, U.S. Pat. No. 8,133,269 and WO2012031916 it is known that $H_2O_2$ reduces or inactivates LPS in gelatin. However, we now observe a surprising synergetic TRITON X100 and $H_2O_2$ effect.

Example 15

Gelatin and TRITON X100 Variation and Effect on LPS Purification
Gelatin solutions with different concentions of dissolved gelatin were mixed at different concentrations of TRITON X-100 under constant mixing with a speed of 750 rpm and at a temperature of 55 to 57.5° C. for 30 minutes. The mixture was then filtered over two 3M ZetaCarbon filter cartridges, of type R55s. The filtrate is collected for direct LPS analysis, or frozen at −20° C. and freeze dried using a Christ Alpha 2-4LD Plus freeze-dryer (MartinChrist, Germany). Freeze-drying vacuum conditions: 0.04 mbar and −87° C. for at least 24-48 hours until the solutions are dried to a moisture content of around 4-6%. No moisture correction was done before endotoxin analysis.

TABLE 15

Gelatin and Triton X100 variation and effect on LPS purification

| Sample | Initial LPS level (EU/g) | Gelatin w/w % | Triton X100 w/w % | Purified LPS level (EU/g) |
|---|---|---|---|---|
| 1 | 1149 | 13 | 0.3 | 5 |
| 2 | 4439 | 13.8 | 0.32 | 29 |
| 3 | 4179 | 15.5 | 0.38 | 32 |
| 4 | 4921 | 12.9 | 0.32 | 15 |
| 5 | 10074 | 20.4 | 0.4 | 10 |
| 6 | 9565 | 22 | 0.5 | 13 |
| 7 | 11467 | 20.4 | 0.4 | 8 |
| 8 | 10376 | 21.6 | 0.4 | 26 |

The invention claimed is:

1. A method of removing lipopolysaccharide from an aqueous medium comprising gelatin and lipopolysaccharides, said method comprising the steps of:
 1) providing an aqueous medium comprising at least 2 w/w % gelatin and lipopolysaccharides,
 2) adding to the aqueous medium 0.01-1.5 w/w % of a micelle-forming surfactant,
 3) contacting the medium of step 2) with a solid adsorbent,
 4) separating the solid adsorbent of step 3) from the medium,
 5) recovering the aqueous medium comprising the gelatin, wherein each of the steps 1)-5) are performed at a temperature of 68° C. or less, said temperature being below the cloud point of the micelle-forming surfactant, at least steps 2) and 3) being performed at a temperature of at least 30° C.

2. The method of 1, wherein the surfactant is represented by the formula

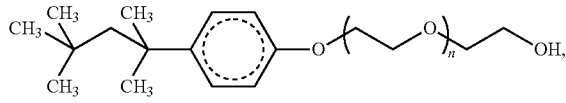

whereby n=on average 9.5 or

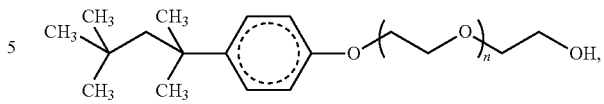

whereby n=on average 12.5, or mixtures thereof.

3. The method of claim 1, wherein the solid adsorbent comprises activated carbon.

4. The method of claim 1, wherein each of the steps 1)-5) are performed at a temperature of 60° C. or less.

5. The method of claim 1, wherein at least steps 2) and 3) are performed at a temperature of at least 45° C.

6. The method of claim 1, wherein each of steps 1)-5) are performed at a temperature of at least 45° C.

7. The method of claim 1, wherein the pH of the medium in step 1) is between 3.5 and 9.0.

8. The method of claim 1, wherein the aqueous medium in step 1) comprises at least 8 w/w % dissolved gelatin.

9. The method of claim 1, wherein the weight ratio of gelatin to added micelle-forming surfactant is 50-5:1.

10. The method of claim 1, wherein step 2) comprises incubating the medium for 1 minute to 1 hour after adding the surfactant.

11. The method of claim 1, wherein the method is free of a centrifugation step.

12. The method of claim 1, wherein the aqueous medium has a salt content 100 mM or less during steps 1)-5).

13. The method of claim 1, wherein the aqueous medium is free of acetone and/or alcohol in steps 1)-5).

14. The method of claim 1, wherein the aqueous medium in step 1) has a lipopolysaccharide content of 1500 EU/g dry weight of gelatin or less.

15. Aqueous medium comprising at least 2 w/w % gelatin obtainable by the method according to claim 9, said medium having a salt content of 100 mM or less, the aqueous medium being free of acetone and quaternary ammonium salts.

* * * * *